United States Patent [19]

Reimer

[11] Patent Number: 5,618,256
[45] Date of Patent: Apr. 8, 1997

[54] DEVICE FOR ARRANGEMENT IN VAGINA FOR PREVENTION OF INVOLUNTARY URINATION WITH FEMALES AND AN APPLICATOR FOR USE IN INSERTION OF THE DEVICE

[75] Inventor: Lotte Reimer, Kokkedal, Denmark

[73] Assignee: Coloplast A/S, Germany

[21] Appl. No.: 331,632

[22] PCT Filed: Aug. 19, 1994

[86] PCT No.: PCT/DK94/00311

§ 371 Date: Nov. 7, 1994

§ 102(e) Date: Nov. 7, 1994

[87] PCT Pub. No.: WO95/05790

PCT Pub. Date: Mar. 2, 1995

[30] Foreign Application Priority Data

Aug. 20, 1993 [DK]  Denmark .................................. 0951/93

[51] Int. Cl.⁶ ...................................................... A61F 2/00
[52] U.S. Cl. ...................................... 600/29; 128/DIG. 25
[58] Field of Search ................. 600/29–32; 128/DIG. 25

[56] References Cited

U.S. PATENT DOCUMENTS

| | | | |
|---|---|---|---|
| 3,554,184 | 1/1971 | Habib | 128/1 |
| 4,019,498 | 4/1977 | Hawtrey et al. | 128/1 |
| 4,139,006 | 2/1979 | Corey | 128/127 |
| 5,036,867 | 8/1991 | Biswas | 128/885 |

FOREIGN PATENT DOCUMENTS

| | | | |
|---|---|---|---|
| 0264258 | 4/1988 | European Pat. Off. | 600/29 |
| 2698781 | 6/1994 | France | 600/30 |
| 2147809 | 9/1983 | United Kingdom . | |
| 4013223 | 6/1994 | WIPO | 600/29 |

*Primary Examiner*—Angela D. Sykes
*Assistant Examiner*—John P. Lacyk
*Attorney, Agent, or Firm*—Ostrolenk, Faber, Gerb & Soffen, LLP

[57] ABSTRACT

A device for prevention of involuntary urination in a female has an elastic body (21) designed for arrangement in the vagina for compressive action on and support of the neck of the bladder. The body (21) is made of a compressible material and comprises at least two projecting legs (23) joined in a flexible base (22) and is dimensioned in such a way that in the non-deformed state of the body of the longest distance between the free ends of at least two legs exceeds the distance between the anterior wall and the posterior wall of the vagina. After the insertion of the body into the vagina in an elastically deformed stated with the legs bent in a direction towards each other, an active pressure is thus exerted on the bladder neck. On their mutually facing sides, the legs are designed in such a way that in the elastically deformed insertion state they come into mutual contact for the provision of an increased elastic force of restitution. An applicator for insertion of the device includes an elongated member having a proximal end and a substantially rod-shaped distal end portion for abutment with a bevel or a recess (24) formed in the angle between the legs of the device.

21 Claims, 5 Drawing Sheets

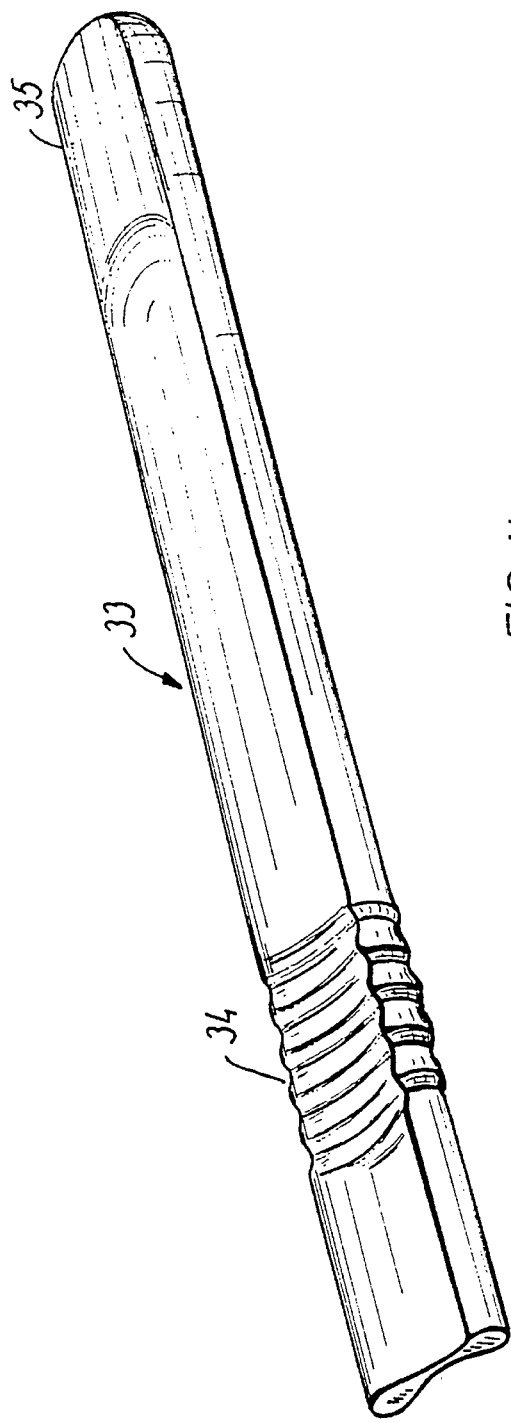
FIG.14
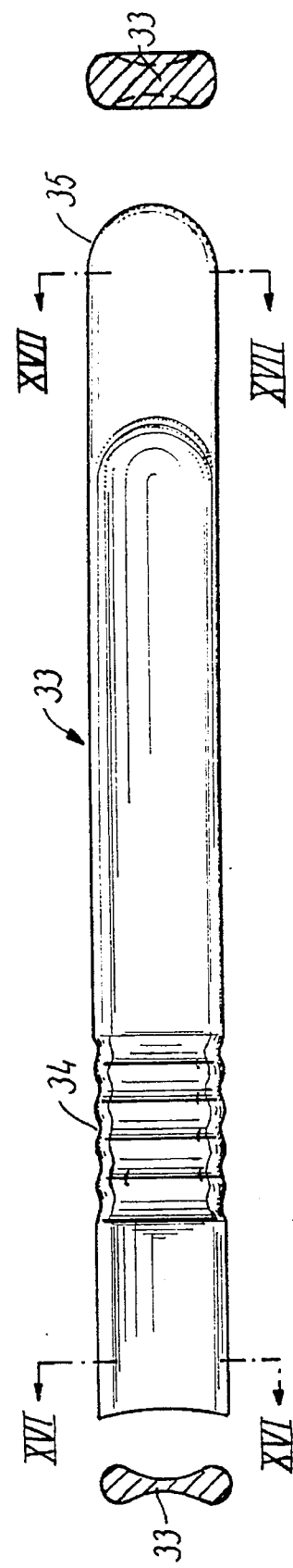
FIG.17
FIG.15
FIG.16

5,618,256

DEVICE FOR ARRANGEMENT IN VAGINA FOR PREVENTION OF INVOLUNTARY URINATION WITH FEMALES AND AN APPLICATOR FOR USE IN INSERTION OF THE DEVICE

BACKGROUND OF THE INVENTION

The present invention relates to a device for prevention of involuntary urination in a female, comprising a body designed for arrangement in the vagina and made of an elastic material for compressive action on and support of the neck of the bladder.

Stress incontinence is a nuisance experienced by up to one third of all women at one time or another during their lives.

Stress incontinence is often caused by a weakening or lack of control of the musculature of the pelvic floor, which results in the lack of support of the bladder neck and closure of the urethra.

Severe cases of stress incontinence are normally relieved by surgical intervention, while minor cases of stress incontinence can often be fully or partially relieved by training or retraining of the pelvic musculature.

Training or retraining of a pelvic muscle may, however, extend over many months and, as mentioned, may not in all cases relieve the problem completely.

It is therefore of great importance to find a product which can relieve stress incontinence.

The use of sanitary towels and napkins for relieving the inconveniences connected with involuntary urination is generally known. This, however, is a method associated with great disadvantages for the woman, as the sanitary towels are unhandy and voluminous, among other things.

Besides, it is known that stress incontinence may be relieved by the use of a tampon-like device which is arranged in the vagina for compressive action and support of the neck of the bladder.

Such a device for relief of stress incontinence is known from, for example, U.S. Pat. No. 4,019,498. This device consists of a body of compressible elastic material which is compressed and then placed in a bag. The bag with the body is inserted in the vagina, whereupon the bag is punctured. The body will then press against the neck of the bladder and in reality block the urethra. This method partly involves a cost-increasing component—the bag—and partly there is a risk of damaging the vagina and adjacent tissue when puncturing the bag.

Furthermore, it is impossible or difficult to adjust the position of the body after mounting in the vagina. Additionally, the body acts purely by the compressibility of the material, for which reason it is necessary to manufacture it in several different sizes.

EP-A-363421 also describes a device for arrangement in a woman's vagina with the object of relieving incontinence. This device also has the disadvantage that it acts as a support to the bladder neck merely in consequence of the compression taking place depending on the size of the vagina and the size of the body.

It is therefore also in this case necessary to manufacture different sizes to compensate for the different vaginal diameters.

Finally, EP-A-264258 describes an incontinence device—specifically for use in vaginal and rectal prolapse—designed as a U-shaped elastic body, which acts by lifting the neck of the bladder, wherein, after being arranged relatively far into the vagina close to the cervix, the body returns to its original position, and one leg of the U which is designed with a forked structure, bears against the bladder/neck of the bladder which is lifted, whereby continence is obtained.

This is thus a relatively rigid structure, which is also designed in rather large dimensions.

This device, as well, is required to be manufactured in different sizes to compensate for the different vaginal diameters, as its lift is exclusively due to its shape, just as it is uncomfortable to wear owing to its rigid and fairly large structure.

A common feature of the above incontinence products is thus that it is necessary to manufacture the product in many different sizes to compensate for the various vaginal diameters.

This is partly economically inappropriate, and partly the body will not have an optimum function even after careful selection of size according to a woman's vaginal diameter, as the support by the bodies of the bladder neck will vary according to the physical posture of the woman and the state of tension of her pelvic muscle. There is thus a great risk that by use of the above-mentioned devices, the woman will still suffer from involuntary urination, and/or that the device will inconvenience, cause pain or even damage the vaginal mucuos membrane, when the woman is in physical movement or tightens her pelvic musculature.

Thus, the known devices are economically unsuitable, just as they do not have an optimum function throughout their service life.

SUMMARY OF THE INVENTION

It is the object of the present invention to provide a device which comfortably relieves the nuisances indicated and thus secures the woman an optimum support regardless of her physical condition and which is at the same time easy to handle.

The device according to the present invention is characterized in that the body is compressible and comprises at least two projecting legs joined in a flexible base and is dimensioned in such a way that in the non-deformed state of the body, the longest distance between the free ends of at least two legs exceeds the distance between the anterior wall and the posterior wall of the vagina, so that after the insertion of the body into the vagina in an elastically deformed state with the legs bent in a direction towards each other, an active pressure is exerted on the neck of the bladder, whereby the legs on the mutually facing sides are designed to come into contact with each other in said elastically deformed insertion state for the provision of an increased elastic force of restitution.

When using the device according to the invention, the compressive and elastic properties of the body are thus utilized together with its properties of restitution, the latter property arising when the legs; of the body are pressed towards each other and will attempt to straighten out after insertion into the vagina, Thus the neck of the bladder is partly supported by the action of the expansion force caused by compression of the body's material in the vagina between the anterior and posterior walls of the vagina and partly by the action of the force of restitution because the folded/bent-in body will attempt to straighten out between said walls.

The combination of the force of restitution and the force of expansion ensures that the product adapts to the varying spatial conditions in the vagina and always provides support for the bladder neck without blocking the urethra. The combination of the two forces also ensures that the product does not become unnecessarily large.

It will thus be possible to keep the resulting support of the bladder neck more stable in case of variations of the vaginal diameter than with the known products.

This means that by use of the device according to the invention, it is possible to obtain a substantially optimum support of the bladder neck without risking exposure of the user to substantial inconveniences or pain or risks of damage to the vaginal mucous membrane.

Additionally, as a consequence of the above, it is possible to manage with a smaller number of sizes for the same user group, just as the product will be easier to insert and remove, as the device has smaller dimensions than the known ones to obtain a more optimum support.

As the body according to the present invention will spontaneously bend in the flexible base in case of folding, the body is easy to handle and to use correctly by the user herself.

Preferably, the device comprises two or three, particularly two, projecting legs which project at a mutual angle of more than about 30°, especially between 90° and 150°.

The device according to the invention may be provided with projecting legs which have a circular cross-section or are wedge-shaped in their outer shape.

In another preferred embodiment, the legs may be provided with a recess on the side facing the urethra and the neck of the bladder and have cushions formed on the opposite side. This makes it possible for the body to cradle the urethra/bladder neck, and it achieves greater compressive strength.

Additionally, on the side intended to face away from the urethra, the body may be provided with ribs in the flexible base periphery. This achieves a greater spring effect.

As a further possibility, the body may be hollow.

This has the result that the body cradles the urethra, as it is compressed most easily at the middle, and as the cross-section of the vagina is substantially shaped like a figure of eight, for which reason the body bears against the walls of the vagina to a higher degree. Additionally, the body need not be oriented at insertion.

The body may additionally be coated fully or partially with an elastic polymer film, such as polyethylene, polypropylene or polyvinyl chloride.

By coating with an elastic film, for example in the flexible base area, it is thus possible to increase the force of restitution of the body without changing the compressive properties of the legs.

The device according to the invention may be made of one or more materials, preferably comprising porous materials selected among polyvinyl alcohol or polyurethane, and wherein the compressive strength of the body is in the interval of 5–40N—preferably 10–20N—at a compression of the body to 50% of its thickness measured before compression.

The force of restitution of the body is in the interval of 1–10N—preferably 1–5N. The density is in the interval of 0.15–0.30 g/cm$^3$—preferably about 0.20 g/cm$^3$.

The body may be provided with a bevel or recess in the angle between the projecting legs to optimize the abutment of an applicator in connection with arrangement of the body in the vagina.

The invention also relates to an applicator for use at insertion of a device according to the invention provided with such recess, which applicator is characterized in that it comprises an elongated member having a proximal end and a substantially rod-shaped distal end portion for abutment with said bevel or recess.

DESCRIPTION OF THE DRAWINGS

The invention will now be described in further detail below with reference to the drawing, in which

FIGS. 14–17 show an embodiment of an applicator for use in the arrangement of the device in the vagina, and FIG. 18 another applicator embodiment.

DETAILED DESCRIPTION OF THE DRAWINGS

Figure 1:
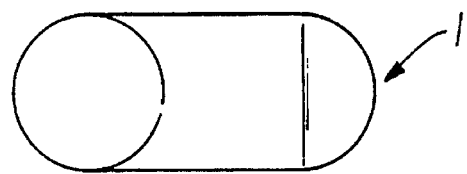
FIGS. 1–3 show a front and a side elevation and a perspective view of a first embodiment of the device.
Figure 2:
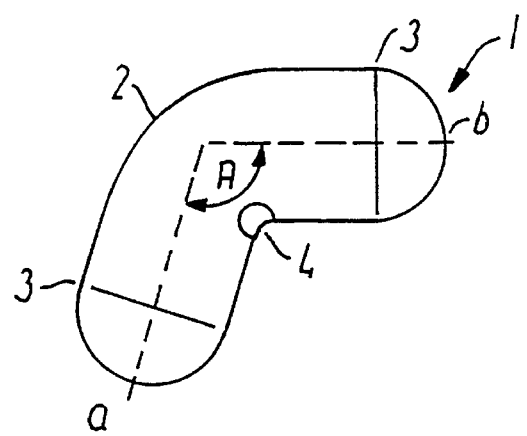
Figure 3:
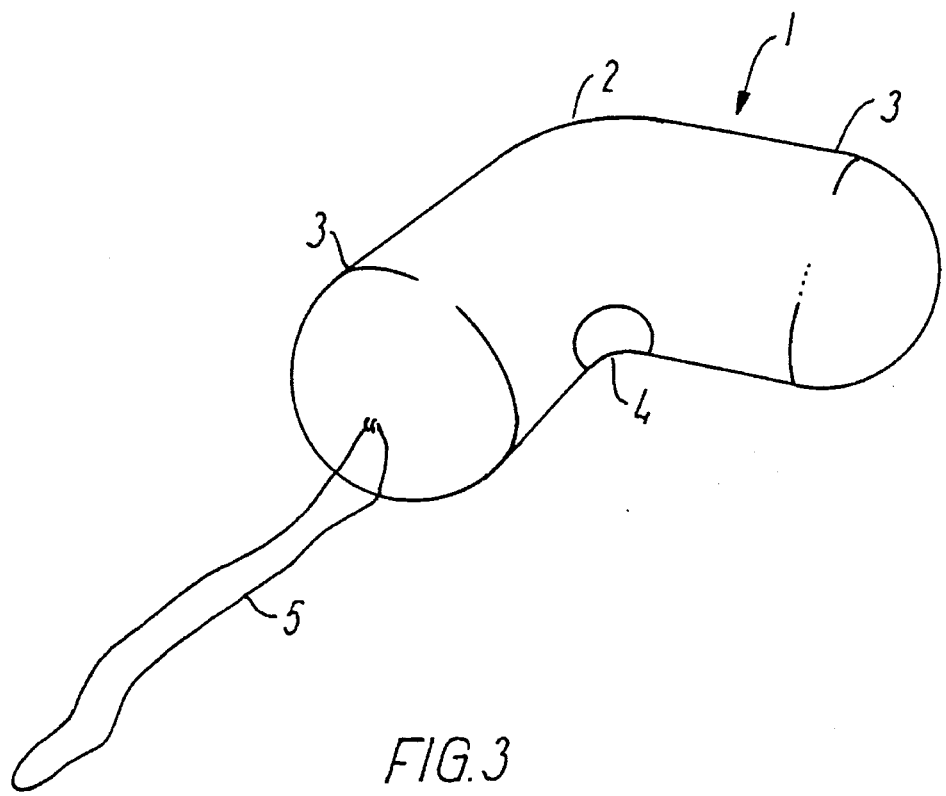

FIGS. 1–3 show a body 1 having a flexible base 2 and two projecting legs 3 positioned in the same plane. The legs 3 have a circular cross-section, but may also have other cross-sectional shapes, such as oval, rectangular, etc.

The angle A between the two legs 3, measured between their axes of symmetry a and b is in the interval of 30°–180°, preferably 90°–150°, and depends on the length of the legs 3. Thus, a large angle renders possible a shortening of the length of the legs—all other things being equal—to obtain the same supporting effect.

The surface of the body 1 is smooth, and the angle between the two legs 3 may accommodate a plateau, a bevel or a recess 4, which an applicator (FIG. 14) may abut to facilitate arrangement of the body in the vagina. One leg or both legs 3 may be provided with a string 5 to facilitate removal of the body from the vagina and insertion of the body into the vagina in connection with the use of an applicator.

The diameter of the legs 3 of the body and the flexible base 2 is in the interval of 20–50 mm, preferably 25–35 mm, while the length of the legs 3, where they are measured as the distance between the end point (a) of a leg and the point (b) determined as the point in which the axes of symmetry of the legs intersect each other, is in the interval of 30–70 mm, preferably 40–50 mm, these dimensions measured with the device 1 in a humidified state.

Before arrangement of the body 1 in the vagina, it is humidified, and the two legs are bent towards each other and pressed into the vagina with the arcuate portion first, where the legs will attempt to unfold and the compressed material will seek back to its state of rest. One leg 3 will press against the anterior wall of the vagina and against the bladder neck and support it, while the other leg 3 bears against the posterior vaginal wall.

The body 1 will follow the movements and dimensional changes occurring in the vagina, partly as a consequence of compression/decompression and partly owing to the force of restitution deriving from the two legs 3 of the body.

Figure 4:
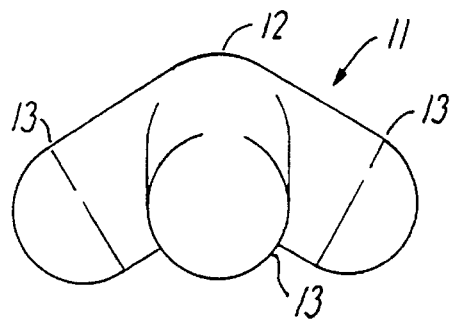
FIGS. 4–6 show an embodiment having three legs.
Figure 5:
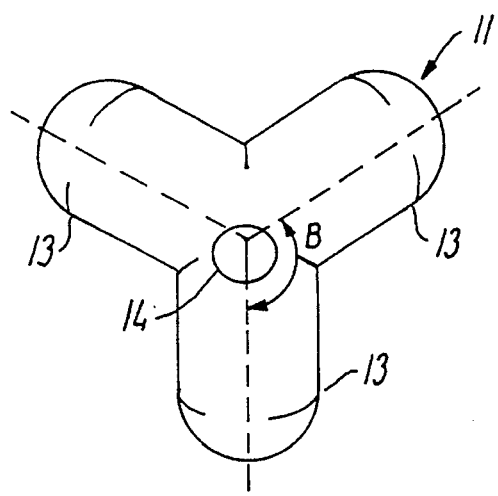
Figure 6:
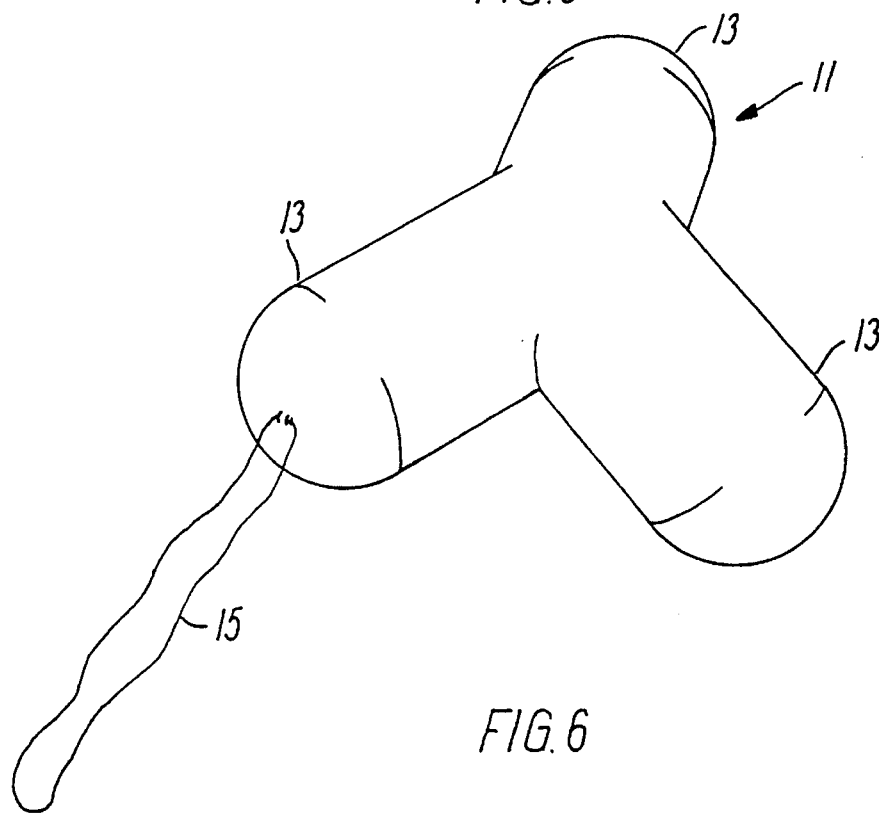
Figure 7:
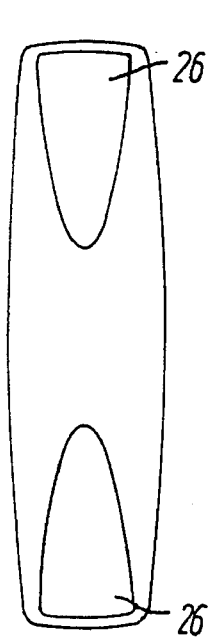
FIGS. 7–12 show a third embodiment of the device.
Figure 8:
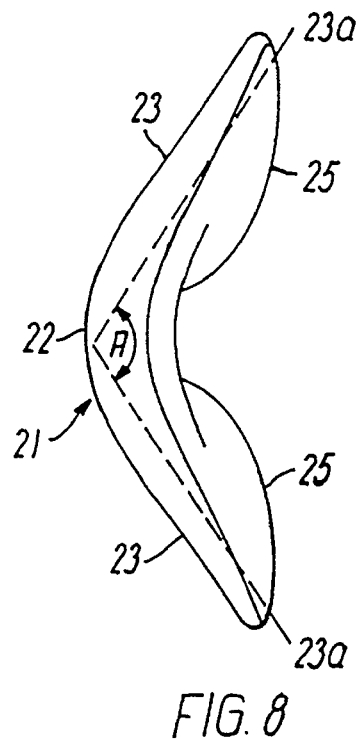
Figure 9:
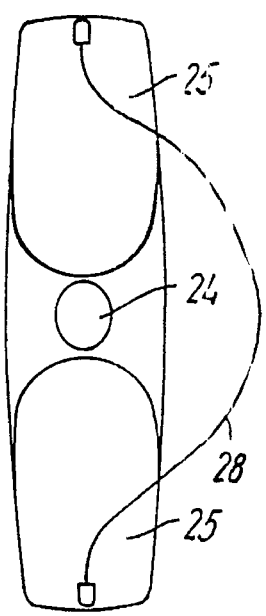
Figure 10:
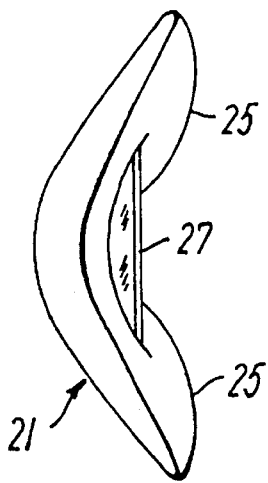
Figure 11:
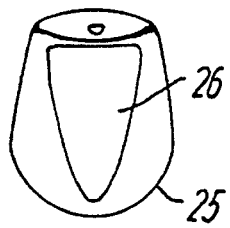
Figure 12:
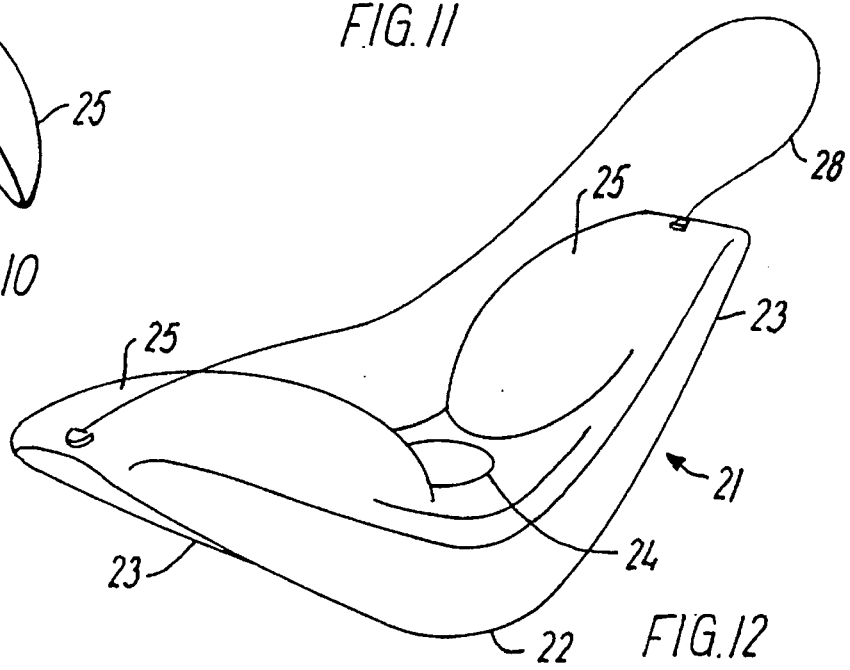

FIGS. 4–6 show another embodiment, wherein the body 11 is provided with three legs 13, but otherwise has the same characteristic features as the one shown in FIGS. 1–3.

The angle B between two legs measured from above (FIG. 5) is 120°.

When arranging this embodiment in the vagina, there is less tendency for the body 11 to "overturn", just as it is easier to position the body, as it need not be oriented.

The device 11 may also be manufactured with more than three legs 13 so that it almost assumes the characteristic of an "octopus".

When using an applicator as shown in FIGS. 14–18, it is made to abut the recess 14 of the body 11, and the string 15 from the latter is pulled up over the other end of the applicator.

FIGS. 7–12 show a third embodiment of the body 21. Here shown with two legs 23, but could well have three or more legs.

Each leg 23 flattens out towards its end pole 23a to end in a wedge-like shape. This shape results in a smaller tendency for the body 21 to "overturn". Each leg 23 is provided with a cushion 25 constituting an integral part of the body 21. The cushion 25 is rounded in its shape and is arranged on the surface of the body 21 facing away from urethra. Providing the body 21 with such a bulge 25 results in higher compressive strength. Opposite to this bulge—on the outer side of the body 21—there is possibly and primarily towards the front a recess 26 in each leg 3. The recess 26 causes the body 21 to cradle the urethra and imparts greater stability.

Additionally, on the side intended to face away from the urethra, the body 21 may be provided with ribs 27 at the periphery of the flexible base 22 and possibly extending fully or partially along the legs 23. This achieves a greater effect of restitution.

At the inner side of the flexible base 22, i.e., at the surface facing the opening of the vagina, a bevel, recess or shelf 24 serving as an abutment surface for an applicator 33 as shown in FIGS. 14–18 may possibly be provided. The distal insertion end of the applicator is then positioned on the abutment surface 24. A string 28 fastened to each leg 3 is pulled back, whereby the body 21 folds about the applicator.

The body 21 is then inserted into the vagina by means of the applicator simultaneously with maintaining the pull in the string 28, and after positioning, the applicator is removed simultaneously with a cessation in the pull of the string 28. Then the body 21 will attempt to unfold in the same manner as described above. All other things being equal, the cushions 25 will impart greater compressive strength to the body 21.

The thickness of the legs 23 of the body and the flexible base 22 is in the interval of 20–50 mm, preferably 25–35 mm, while the length of the legs 23 these being measured as the distance between the end point (a) of a leg and the point (b) determined as the point at which the axes of symmetry of the legs intersect each other, is in the interval of 30–70 mm, preferably 40–50 mm, and where these dimensions are measured with the device 21 in a humidified state.

The width of the device is in the interval of 10–40 mm, preferably 15–25 mm (also measured in a humidified state).

Figure 13:
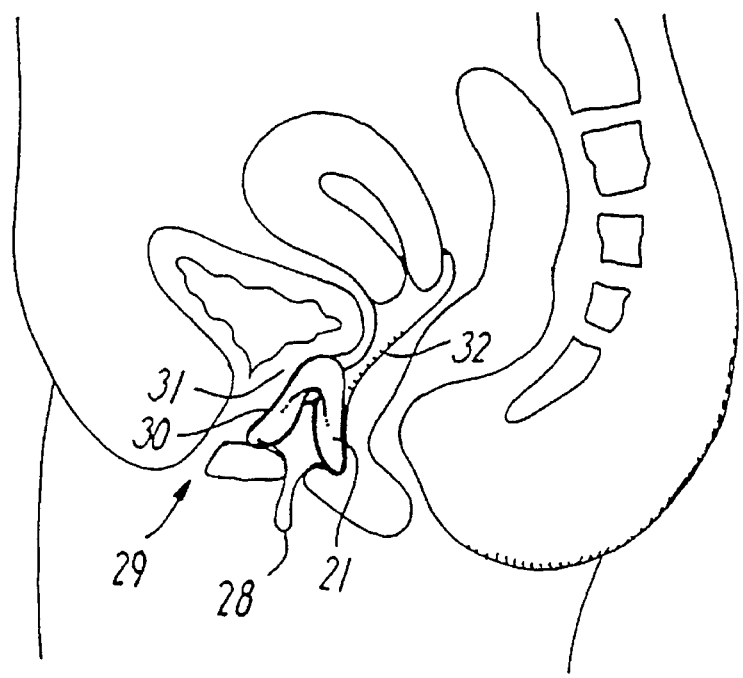
FIG. 13 shows the arrangement of the device in the vagina for control of incontinence, shown in a sagittal cross-section.

FIG. 13 shows the device of FIGS. 7–12 in its position of use.

When the body 21 is positioned in the vagina 29, one leg with its full surface bears against the vaginal anterior wall 30 and supports the neck 31 of the bladder, whereby continence is achieved. The other leg bears against the posterior wall 32 of the vagina. Thus, the device does not completely fill the vagina.

The compressive strength of the body is in the interval of 5–40N—preferably 10–20N—at a compression of the body to 50 percent of its thickness measured before compression. The force of restitution of the body is in the interval of 1–10N—preferably 1–5N (said values for the device in a humidified state).

The density of the material is in the interval of 0.15–0.30 g/cm$^3$, preferably about 0.2 g/cm$^3$.

Suitable materials for forming the above embodiments of the device are preferably formalized polyvinyl alcohol and polyurethane, but other materials may also be applied.

A suitable polyurethane material is prepared by mixing a prepolymerized polyurethane with water. 0.5–3 percent, preferably 1–2 percent, of a surface active additive has been added to the aqueous phase. A suitable surface-active additive is, for example, Emulgade 1000Ni from Henkel. The polyurethane may be Hypol 2002 from Hampshire Chemical Corporation. The mixing ratio between the polyurethane component and the aqueous phase is selected so that there is an excess of polyurethane of 0–20 percent—preferably 8–12 percent. The material has the property that it expands by about 30 percent when it is humidified, and it is a compressible, elastic material.

By manufacturing the body from this material, it is possible to obtain a saving on packaging, as the body takes up less space in a dry state than in the humidified state of use, and the body possesses good material properties rendering it pleasant for the user to utilize the body.

FIGS. 14–18 show two embodiments of an applicator for use in the insertion of the above-described embodiments of the incontinence device into the vagina. In FIGS. 14–17, the applicator comprises an elongated member 33 having a proximal end forming a finger grip 34 and a substantially distal end portion 35 being formed for abutment with the recess 24 at the rearwards facing side of the base 22 between the legs 23.

In the embodiment of FIGS. 14–17, the member 33 has a substantially double concave, relatively flat cross-sectional profile along substantially most of its length. At the proximal end, the finger grip 34 is formed by means of a rib shape. To reduce friction and facilitate removal of the applicator after arrangement of the device in the vagina, the distal end portion 35 is formed with smooth, plane or possibly slightly convex sides of the cross-sectional profile, as shown in FIG. 17.

Figure 18:
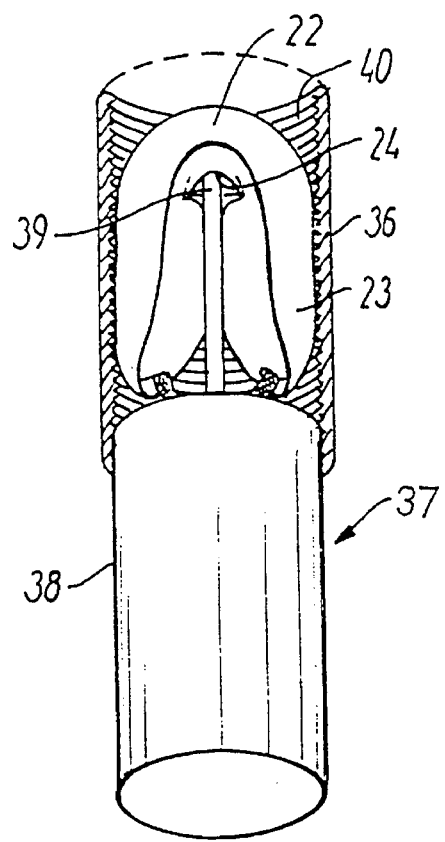

In the embodiment of FIG. 18, the applicator comprises a cylindrical body 36 which is open at both ends and formed for receiving an incontinence device as shown in FIGS. 7–12 in its elastically compressed insertion state with the flexible base 22 facing towards one open end of the member 36, which end is positioned in the opening of the vagina when the applicator is used. An elongated member 37 comprises at its proximal end a piston-like element 38, which fits the internal diameter of the cylindrical body 36 and is intended for insertion at the opposite end of the body 36, and a substantially rod-shaped distal end portion 39 which may be formed in the same manner as in the embodiment of FIGS. 14–17. The piston-like element comprises a handle part projecting outside the applicator. In both embodiments, the distal insertion end 35, 39, respectively, may be designed for abutment also with the recesses 4 or 14 in the embodiments shown in FIGS. 1–5. At a pull in the string 5, 15 or 28, the body will fold and be squeezed around the applicator, whereby the insertion is facilitated. In the embodiment of FIG. 18, the cylindrical body 36 may have an internal rib-shaped wall 40 to facilitate insertion, whereby the contact surface against the elastically deformed incontinence device is reduced and friction is lowered. The same effect may be obtained by means of a PTFE coating on the internal wall of the body.

I claim:

1. A device for prevention of involuntary urination in a female, comprising:

an elastic body designed for arrangement in a human vagina for compressive action on and support of the neck of the bladder, the body being made of a compressible material;

said body including at least two projecting legs joined in a flexible base and dimensioned in such a way that in the non-deformed state of the body, the longest distance between free ends of the at least two legs exceeds the distance between the anterior wall and the posterior wall of the vagina, so that after insertion of the body into the vagina in an elastically deformed state with the legs bent in a direction towards each other, an active pressure is exerted on the neck of the bladder; and the compressible body is made of a porous material having such a compressibility that at a compression of each leg to 50 percent of its total thickness measured before compression, the compressive strength of the body is in the interval of 5–40N, so that, by deformation of the legs in the elastically deformed insertion state to come into contact with each other on the mutually facing sides, the compressible material is compressed to provide an increased elastic force of restitution in the interval of 1–10N.

2. A device according to claim 1, in which the legs diverge at an angle, measured between axes of symmetry of the legs, of more than about 30 degrees.

3. A device according to claim 1, in which an angle (a) between the legs is smaller than 180°.

4. A device according to claim 3, in which the angle is in the range of 90°–150°.

5. A device according to claim 1, in which the body comprises three legs.

6. A device according to claim 1, in which the legs and the base have a substantially circular cross-section.

7. A device according to claim 1, in which the legs are wedge-shaped.

8. A device according to claim 1, in which on a side which is intended to face the urethra when the body is inserted in the vagina, each leg is provided with a recess and on the opposite side with a cushion constituting an integral part of the leg.

9. A device according to claim 8, in which on another side intended to face away from the urethra, the body is provided with ribs in the periphery of the part comprising the flexible base and fully or partially on the periphery of the legs, which ribs constitute an integral part of the device.

10. A device according to claim 1, in which the body is hollow.

11. A device according to claim 1, in which the body is fully or partially coated with an elastic polymer film selected from the group: polyethylene, polypropylene and polyvinyl chloride.

12. A device according to claim 1, in which the body is formed in polyurethane or polyvinyl alcohol.

13. A device according to claim 1, in which the device is manufactured from a material the density of which is in the interval of 0.15–cm 0.30 g/cm$^3$.

14. A device according to claim 1, in which the device comprises a bevel or a recess in the angle between the projecting legs, on which bevel or recess an applicator is adapted to abut for arrangement of the device in the vagina.

15. A device according to claim 14, including an applicator for use in the insertion into the vagina of the device, the applicator comprising an elongated member with a proximal end and with a substantially rod-shaped distal end portion for abutment with said bevel or recess.

16. A device according to claim 15, in which the proximal end is provided with a finger grip.

17. A device according to claim 15, in which the proximal end forms a piston-like element, which fits into one end of a substantially cylindrical body which is open at both ends and is formed for receiving said device in its elastically deformed insertion state with the flexible base facing towards the other open end of the body, whereby the piston-like element comprises a handle part projecting outside the cylindrical body.

18. A device according to claim 17, in which an internal wall of the cylindrical body is designed for reducing friction against the device.

19. A device according to claim 1, in which a distal end portion of the body is designed for reducing friction against the mutually facing sides of the legs of the device.

20. A device according to claim 1, in which the compressive strength of the body is in the interval of 10–20N, and the compressible material is compressed to provide an increased elastic force of restitution in the interval of 1–5N.

21. A device according to claim 1, in which the density of the material is about 0.20 g/cm$^3$.

* * * * *